(12) United States Patent
Cirillo et al.

(10) Patent No.: US 6,297,381 B1
(45) Date of Patent: Oct. 2, 2001

(54) AROMATIC HETEROCYCLIC COMPOUNDS AS ANTI-INFLAMMATORY AGENTS

(75) Inventors: Pier F. Cirillo, Woodbury; Eugene R. Hickey, Danbury, both of CT (US); John R. Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/503,385

(22) Filed: Feb. 14, 2000

Related U.S. Application Data

(60) Provisional application No. 60/124,147, filed on Mar. 12, 1999.

(51) Int. Cl.$^7$ .................. C07D 213/02; C07D 333/00; A61K 31/381
(52) U.S. Cl. ................. 546/1; 549/68; 549/70; 514/438; 514/444; 514/447; 514/448
(58) Field of Search ................. 514/444, 438, 514/447, 448; 546/1; 549/68, 70

(56) References Cited

U.S. PATENT DOCUMENTS

| | | |
|---|---|---|
| 4,105,766 | 8/1978 | Alexander . |
| 4,435,567 | 3/1984 | Lugosi et al. ............... 544/165 |
| 5,162,360 | 11/1992 | Creswell . |
| 5,686,455 | 11/1997 | Adams et al. ............... 514/256 |
| 5,739,143 | 4/1998 | Adams et al. ............... 514/275 |
| 5,777,097 | 7/1998 | Lee et al. ............... 536/24.31 |
| 5,783,664 | 7/1998 | Lee et al. ............... 530/350 |
| 5,859,041 | 1/1999 | Liverton et al. ............... 514/396 |
| 5,869,043 | 2/1999 | McDonnell et al. ............... 424/94.1 |
| 5,871,934 | 2/1999 | Lee et al. ............... 435/7.1 |
| 5,916,760 | 6/1999 | Goeddel et al. ............... 435/15 |
| 5,948,885 | 9/1999 | Stein et al. ............... 530/224 |

FOREIGN PATENT DOCUMENTS

| | | |
|---|---|---|
| 293 352 | 8/1991 | (DE) . |
| 0 272 866 | 6/1988 | (EP) . |
| 0 395 144 | 10/1990 | (EP) . |
| 0 418 071 | 3/1991 | (EP) . |
| 0 955 293 | 10/1999 | (EP) . |
| 61228444 | 10/1986 | (JP) . |
| WO 93/24458 | 9/1993 | (WO) . |
| WO 94/18170 | 8/1994 | (WO) . |
| WO 94/22866 | 10/1994 | (WO) . |
| WO 96/25157 | 8/1996 | (WO) . |
| WO 97/16442 | 5/1997 | (WO) . |
| WO 97/48697 | 12/1997 | (WO) . |
| 9932111 | * 7/1999 | (WO) . |
| WO 00/43384 | 7/2000 | (WO) . |

OTHER PUBLICATIONS

Application No. 09/484,638 filed Jan. 18, 2000; Cirillo, P. et al; Aromatic Heterocyclic Compound as Antiinflammatory Agents.

Application No. 09/505,582 filed Feb. 16, 2000; Cirillo, P. et al; Compounds Useful as Anti–Inflammatory Agents.

Jagadish C. Sircar, et al; Pyrazolo[5,1–b]quinazolin–9 ones: A New Series of Antiallergic Agents, J. Med. Chem. 1981, 24, 735–742.

Application No. 09/503,263 filed Feb. 14, 2000; Zhang, L. et al; Polycyclo Heterocyclic Derivatives as Antiinflammatory Agents.

* cited by examiner

*Primary Examiner*—Mukund J. Shah
*Assistant Examiner*—Sudhaker B. Patel
(74) *Attorney, Agent, or Firm*—Robert P. Raymond; Anthony P. Bottino; Alan R. Stempel

(57) ABSTRACT

Disclosed are novel aromatic heterocyclic compounds of the formula(I) wherein $Ar_1, Ar_2, L, Q$ and $X$ are described herein. The compounds are useful in pharmaceutic compositions for treating diseases or pathological conditions. Also disclosed are processes of making such compounds.

(I)

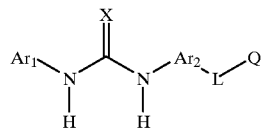

20 Claims, No Drawings

AROMATIC HETEROCYCLIC COMPOUNDS AS ANTI-INFLAMMATORY AGENTS

RELATED APPLICATIONS

This application claims priority to U.S. Provisional Application Ser. No. 60/124,147 filed Mar. 12, 1999.

TECHNICAL FIELD OF THE INVENTION

This invention relates to novel aromatic heterocyclic compounds of formula (I):

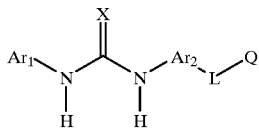

(I)

wherein $Ar_1$, $Ar_2$, X, L and Q are defined below, which inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). An important and accepted therapeutic approach for potential drug intervention in these diseases is the reduction of proinflammatory cytokines such as TNF (also referred to in its secreted cell-free form termed TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45–2081 (Hoffman-LaRoche Inc., Nutley, N.J.) has demonstrated efficacy in various animal models of allergic lung inflammation and acute lung injury. Ro 45–2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitis shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypootheses* 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis. Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dememtia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, J R *Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFN γ (Ablumunits, et al., 1998, *J Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction.

Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol.* 109, 342). The expression of a number of cytokines, including IFN γ has been shown to increase following a delayed type hypersensitivity reaction thus indicating a role for IFNγ in atopic dermatitis (Szepietowski, et al., 1997, *Br J Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ , TNF and IL-2 (Chisari, et al., 1995, *Springer Semin Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the TH 1 phenotype (Sartor 1996, *Aliment Pharmacol Ther.* 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease.

It is yet a further object of the invention to provide processes of preparation of the above-mentioned novel compounds.

DETAILED DESCRIPTION OF THE INVENTION

The present invention is directed to compounds of the formula (I):

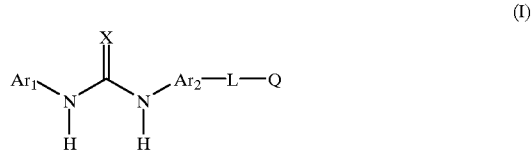

wherein:
Ar$_1$ is a heterocyclic group selected from the group consisting of pyrrole, pyrrolidine, pyrazole, imidazole, oxazole, thiazole, furan, and thiophene; and wherein Ar, may be substituted by one or more R$_1$,R$_2$ or R$_3$;

Ar$_2$ is:
phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three R$_{10}$ groups;

L is a linking group of:
a C$_{1-10}$ saturated or unsaturated branched or unbranched carbon chain;
wherein one or more methylene groups are optionally independently replaced by O,N or S; wherein said linking group is optionally independently substituted with 0–2 oxo groups or one or more $C_{1-4}$ branched or unbranched alkyl which may be substituted by one or more halogen atoms;

Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl and $C_{1-5}$ alkoxyalkyl, phenylamino, wherein the phenyl ring is optionally substituted with one to two groups selected from the group consisting of halogen, $C_{1-6}$ alkoxy, hydroxy or mono- or di-($C_{1-3}$ alkyl)amino, $C_{1-6}$ alkyl-S(O)$_t$ and phenyl-S(O)$_p$, wherein the phenyl ring is optionally substituted with one to two groups selected from the group consisting of halogen, $C_{1-6}$ alkoxy, hydroxy and mono- or di-($C_{1-3}$ alkyl)amino;

$R_1$ is selected from the group consisting of:

(a) $C_{3-10}$ branched or unbranched alkyl, which may optionally be partially or fully halogenated, and optionally substituted with one to three phenyl, naphthyl or heterocyclyl groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocyclyl, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, $NH_2C(O)$ and di($C_{1-3}$)alkylaminocarbonyl;

(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;

(c) $C_{3-10}$ branched alkenyl which may optionally be partially or fully halogenated, and which optionally substituted with one to three $C_{1-5}$ branched or unbranched alkyl, phenyl, naphthyl or heterocyclyl groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclyl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkoxy which is optionally partially or fully halogenated, $NH_2C(O)$, mono- or di($C_{1-3}$)alkylaminocarbonyl;

(d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

(e) cyano; and, (f) methoxycarbonyl, ethoxycarbonyl and propoxycarbonyl;

$R_2$ is selected from the group consisting of:

hydrogen, $C_{1-6}$ branched or unbranched alkyl which may optionally be partially or fully halogenated, acetyl, aroyl, $C_{1-4}$ branched or unbranched alkoxy which may optionally be partially or fully halogenated, halogen, methoxycarbonyl and phenylsulfonyl;

$R_3$ is:

halogen, —$COOR_4$, —CN, —$CONR_5R_6$ or —$CH_2NHR_7$;

$R_4$ is H or $C_{1-4}$-alkyl;

$R_5$ is hydrogen;

$R_6$ is methyl;

$R_7$ is hydrogen, methyl or —$C(O)R_8$;

$R_8$ is hydrogen or methyl optionally substituted by $N(R_9)_2$ or $COOR_9$;

$R_9$ is $C_{1-6}$-alkyl;

$R_{10}$ is selected from the group consisting of:

a $C_{1-6}$ branched or unbranched alkyl which may optionally be partially or fully halogenated, acetyl, aroyl, $C_{1-4}$ branched or unbranched alkoxy which may optionally be partially or fully halogenated, halogen, methoxycarbonyl and phenylsulfonyl;

m is 0, 1 or 2;

r is 0, 1 or 2 t is 0, 1 or 2

X is O (oxygen) or S (sulfur) and pharmaceutically acceptable derivatives thereof.

A preferred subgeneric aspect of the invention comprises compounds of the formula(I) wherein $Ar_1$ is selected from the group consisting of:

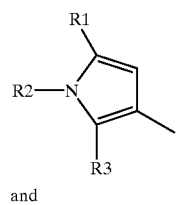 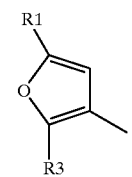 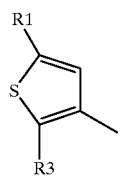

and

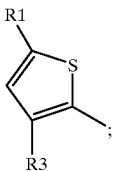

more preferred are compounds of the formula (I) wherein Ar₂ is naphthyl, tetrahydronaphthyl, indanyl or indenyl.

An even more preferred subgeneric aspect of the invention comprises compounds of the formula(I) wherein Ar₂ is naphthyl.

A yet more preferred subgeneric aspect of the invention comprises compounds of the formula (I), as described in the immediate previous paragraph, wherein:

Ar₂ is 1-naphthyl;

L is $C_{1-6}$ saturated or unsaturated branched or unbranched carbon chain wherein
one or more methylene groups are optionally independently replaced by O,N or S; wherein said linking group is optionally independently substituted with 0–2 oxo groups and one or more $C_{1-4}$ branched or unbranched alkyl which may be substituted by one or more halogen atoms;

$R_1$ is $C_{1-4}$alkyl branched or unbranched, cyclopropyl or cyclohexyl which may optionally be partially or fully halogenated and which may optionally be substituted with one to three $C_{1-3}$ alkyl groups; and $R_3$ is —COOR₄, —CN, —CONR₅R₆ or —CH₂NHR₇.

A further preferred subgeneric aspect of the invention comprises compounds of the formula (I), wherein Ar₁ is 5-tert-butyl-3-thienyl or 5-tert-butyl-3-pyrrolyl.

A still yet further preferred subgeneric aspect of the invention comprises compounds of the formula (I), as described in the immediate previous paragraph, wherein L is $C_{1-5}$ saturated carbon chain wherein one or more methylene groups are optionally independently replaced by O,N or S; and wherein said linking group is optionally independently substituted with 0–2 oxo groups and one or more $C_{1-4}$ branched or unbranched alkyl which may be substituted by one or more halogen atoms and X is O.

Particularly preferred embodiments of L are propoxy, ethoxy, methoxy, methyl, propyl, $C_{3-5}$ acetylene or methylamino each being optionally substituted are described herein.

The following compounds are representative of the compounds of formula(I):

1-[2-Carbomethoxy-5-tert-butyl-3-thienyl]-3-[4-(2-morpholin-4-yl-ethoxy)naphthalen-1-yl]-urea;
1-[2-Methylcarbamoyl-5-tert-butyl-3-thienyl]-3-[4-(2-morpholin-4-yl-ethoxy)naphthalen-1-yl]-urea;
1-[3-Carbomethoxy-5-tert-butyl-2-thienyl]-3-[4-(2-morpholin-4-yl-ethoxy)naphthalen-1-yl]-urea;
1-[2-(N-Glycylaminomethyl)-5-tert-butyl-2-thienyl]-3-[4-(2-morpholin-4-yl-ethoxy)naphthalen-1-yl]-urea;
1-[2-(N-Glycylaminomethyl)-5-tert-butyl-3-thienyl]-3-[4-(2-(cis-2,6-dimethylmorpholin-4-yl)ethoxy)naphthalen-1-yl]-urea;
1-[2-Methylcarbamoyl-5-tert-butyl-3-thienyl]-3-[4-(2-(trans-2,6-dimethylmorpholin-4-yl)ethoxy)naphthalen-1-yl]-urea;
1-[2-Methylcarbamoyl-5-tert-butyl-3-thienyl]-3-[4-(2-(2-dimethylaminomethyldimethylmorpholin-4-yl)ethoxy)naphthalen-1-yl]-urea;
1-[2-Carbomethoxy-5-tert-butyl-3-thienyl]-3-[4-(2-(2-(methoxymethyl)morpholin-4-yl)ethoxy)naphthalen-1-yl]-urea;
1-[2-Carbomethoxy-5-tert-butyl-3-thienyl]-3-[4-(2-(morpholin-4-yl)-1-methylethoxy)naphthalen-1-yl]-urea;
1-[2-Carbomethoxy-5-tert-butyl-3-thienyl]-3-[4-(2-(1-oxothiomorpholin-4-yl)ethoxy)naphthalen-1-yl]-urea;
1-[2-Methylcarbamoyl-5-tert-butyl-3-thienyl]-3-[4-(2-(1-oxothiomorpholin-4-yl)ethoxy)naphthalen-1-yl]-urea;
1-[3-Carbomethoxy-5-tert-butyl-2-thienyl]-3-[4-(2-(1-oxothiomorpholin-4-yl)ethoxy)naphthalen-1-yl]-urea;
1-[2-Carbomethoxy-5-tert-butyl-3-thienyl]-3-[4-(2-(tetrahydropyran-4-yl)ethoxy)naphthalen-1-yl]-urea;
1-[2-Methylcarbamoyl-5-tert-butyl-3-thienyl]-3-[4-(2-(tetrahydropyran4-yl)ethoxy)naphthalen-1-yl]-urea;
1-[3-Carbomethoxy-5-tert-butyl-2-thienyl]-3-[4-(2-(tetrahydropyran-4-yl)ethoxy)naphthalen-1-yl]-urea;
1-[2-Carbomethoxy-5-tert-butyl-3-thienyl]-3-[4-(2-(1-oxo-tetrahydrothiophen-3-yl)ethoxy)naphthalen-1-yl]-urea;
1-[2-Methylcarbamoyl-5-tert-butyl-3-thienyl]-3-[4-(2-(1-oxo-tetrahydrothiophen-3-yl)ethoxy)naphthalen-1-yl]-urea;
1-[2-(N-Acetylaminomethyl)-5-tert-butyl-3-thienyl]-3-[4-(2-(1-oxo-tetrahydrothiophen-3-yl)ethoxy)naphthalen-1-yl]-urea;
1-[3-Carbomethoxy-5-tert-butyl-2-thienyl]-3-[4-(2-(1-oxo-tetrahydrothiophen-3-yl)ethoxy)naphthalen-1-yl]-urea;
1-[2-Methylcarbamoyl-5-tert-butyl-3-thienyl]-3-[4-(3-morpholin-4-yl-propyl)naphthalen-1-yl]-urea;
1-[2-Carbomethoxy-5-tert-butyl-3-thienyl]-3-[4-(morpholin-4-yl-methyl)naphthalen-1-yl]-urea;
1-[2-Carbomethoxy-5-tert-butyl-3-thienyl]-3-[4-(2-pyridin-4-yl-ethyl)naphthalen-1-yl]-urea;
1-[2-Carbomethoxy-5-tert-butyl-3-thienyl]-3-[4-(3-(morpholin-4-yl)propyn-1-yl)naphthalen-1-yl]-urea;
1-[2-Methylcarbamoyl-5-tert-butyl-3-thienyl]-3-[4-(3-(tetrahydropyran-2-yl-oxy)propyn-1-yl)naphthalen-1-yl]-urea;
1-[2-Methylcarbamoyl-5-tert-butyl-3-thienyl]-3-[4-(3-(tetrahydropyran-2-yl-oxy)butyn-1-yl)naphthalen-1-yl]-urea;
1-[2-Carbomethoxy-5-tert-butyl-3-thienyl]-3-[4-(pyridin4-yl-methoxy)naphthalen-1-yl]-urea;
1-[2-Methylcarbamoyl-5-tert-butyl-3-thienyl]-3-[4-(pyridin-4-yl-methoxy)naphthalen-1-yl]-urea;
1-[2-(N-Acetylaminomethyl)-5-tert-butyl-3-thienyl]-3-[4-(pyridin-4-yl-methoxy)naphthalen-1-yl]-urea;
1-[3-Carbomethoxy-5-tert-butyl-2-thienyl]-3-[4-(pyridin-4-yl-methoxy)naphthalen-1-yl]-urea;
1-[2-Carbomethoxy-5-tert-butyl-3-thienyl]-3-[4-(2-pyridin-4-yl-ethoxy)naphthalen-1-yl]-urea;
1-[2-Methylcarbamoyl-5-tert-butyl-3-thienyl]-3-[4-(3-pyridin-4-yl-propoxy)naphthalen-1-yl]-urea;
1-[2-Carbomethoxy-5-tert-butyl-3-thienyl]-3-[4-(2-imidazol-1-yl-ethoxy)naphthalen-1-yl]-urea;
1-[2-Carbomethoxy-5-tert-butyl-3-thienyl]-3-[4-(2-(3,4-dimethoxyphenyl)-ethoxy)naphthalen-1-yl]-urea;
1-[2-Methylcarbamoyl-5-tert-butyl-3-thienyl]-3-[4-(2-(3,4-dimethoxyphenyl)-ethoxy)naphthalen-1-yl]-urea;
1-[3-Carbomethoxy-5-tert-butyl-2-thienyl]-3-[4-(2-(3,4-dimethoxyphenyl)-ethoxy)naphthalen-1-yl]-urea;
1-[2-Methylcarbamoyl-5-tert-butyl-3-thienyl]-3-[4-(pyridin-4-yl-methylamino)naphthalen-1-yl]-urea;
1-[2-Carbomethoxy-5-iso-propyl-3-thienyl]-3-[4-(2-morpholin-4-yl-ethoxy)naphthalen-1-yl]-urea;
1-[2-Methylcarbamoyl-5-cyclohexyl-3-thienyl]-3-[4-(2-morpholin-4-yl-ethoxy)naphthalen-1-yl]-urea;
1-[5-2-Carbomethoxy-5-(2,2,2-trifluoroethyl)-3-thienyl]-3-[4-(2-morpholin4-ethoxy)naphthalen-1-yl]-urea;
1-[2-Carbomethoxy-5-(1-methylcycloprop-1-yl)-3-thienyl]-3-[4-(2-morpholin-4-yl-ethoxy)naphthalen-1-yl]-urea;

1-[2-Carbomethoxy-5-(1-methylcyclohex-1-yl)-3-thienyl]-3-[4-(2-morpholin-4-yl-ethoxy)naphthalen-1-yl]-urea;
1-[2-Carbomethoxy-5-tert-butyl-3-furyl]-3-[4-(2-morpholin-4-yl-ethoxy)naphthalen-1-yl]-urea;
1-[2-Carbomethoxy-5-tert-butyl-3-furyl]-3-[4-(2-(cis-2,6-dimethylmorpholin-4-yl)ethoxy)naphthalen-1-yl]-urea;
1-[2-Carbomethoxy-5-tert-butyl-3-furyl]-3-[4-(2-(trans-2,6-dimethylmorpholin-4-yl)ethoxy)naphthalen-1-yl]-urea;
1-[2-Carbomethoxy-5-tert-butyl-3-furyl]-3-[4-(2-(2-(methoxymethyl)morpholin-4-yl)ethoxy)naphthalen-1-yl]-urea;
1-[2-Carbomethoxy-5-tert-butyl-3-furyl]-3-[4-(2-(morpholin-4-yl)-1-methylethoxy)naphthalen-1-yl]-urea;
1-[2-Carbomethoxy-5-tert-butyl-3-furyl]-3-[4-(2-(1-oxothiomorpholin-4-yl)ethoxy)naphthalen-1-yl]-urea;
1-[2-Carbomethoxy-5-tert-butyl-3-furyl]-3-[4-(2-(tetrahydropyran-4-yl)ethoxy)naphthalen-1-yl]-urea;
1-[2-Carbomethoxy-5-tert-butyl-3-furyl]-3-[4-(2-(1-oxo-tetrahydrothiophen-3-yl)ethoxy)naphthalen-1-yl]-urea;
1-[2-Carbomethoxy-5-tert-butyl-3-furyl]-3-[4-(3-morpholin-4-yl-propyl)naphthalen-1-yl]-urea;
1-[2-Carbomethoxy-5-tert-butyl-3-furyl]-3-[4-(morpholin-4-yl-methyl)naphthalen-1-yl]-urea;
1-[2-Carbomethoxy-5-tert-butyl-3-furyl]-3-[4-(2-pyridin-4-yl-ethyl)naphthalen-1-yl]-urea;
1-[2-Carbomethoxy-5-tert-butyl-3-furyl]-3-[4-(3-(morpholin-4-yl)propyn-1-yl)naphthalen-1-yl]-urea;
1-[2-Carbomethoxy-5-tert-butyl-3-furyl]-3-[4-(3-(tetrahydropyran-2-yl-oxy)propyn-1-yl)naphthalen-1-yl]-urea;
1-[2-Carbomethoxy-5-tert-butyl-3-furyl]-3-[4-(3-(tetrahydropyran-2-yl-oxy)butyn-1-yl)naphthalen-1-yl]-urea;
1-[2-Carbomethoxy-5-tert-butyl-3-furyl]-3-[4-(pyridin-4-yl-methoxy)naphthalen-1-yl]-urea;
1-[2-Carbomethoxy-5-tert-butyl-3-furyl]-3-[4-(2-pyridin-4-yl-ethoxy)naphthalen-1-yl]-urea;
1-[2-Carbomethoxy-5-tert-butyl-3-furyl]-3-[4-(3-pyridin-4-yl-propoxy)naphthalen-1-yl]-urea;
1-[2-Carbomethoxy-5-tert-butyl-3-furyl]-3-[4-(2-imidazol-1-yl-ethoxy)naphthalen-1-yl]-urea;
1-[2-Carbomethoxy-5-tert-butyl-3-furyl]-3-[4-(2-(3,4-dimethoxyphenyl)-ethoxy)naphthalen-1-yl]-urea;
1-[2-Carbomethoxy-5-tert-butyl-3-furyl]-3-[4-(pyridin-4-yl-methylamino)naphthalen-1-yl]-urea;
1-[2-Carbomethoxy-5-iso-propyl-3-furyl]-3-[4-(2-morpholin-4-yl-ethoxy)naphthalen-1-yl]-urea;
1-[2-Carbomethoxy-5-cyclohexyl-3-furyl]-3-[4-(2-morpholin-4-yl-ethoxy)naphthalen-1-yl]-urea;
1-[5-2-Carbomethoxy-5-(2,2,2-trifluoroethyl)-3-furyl]-3-[4-(2-morpholin-4-yl-ethoxy)naphthalen-1-yl]-urea;
1-[2-Carbomethoxy-5-(1-methylcycloprop-1-yl)-3-furyl]-3-[4-(2-morpholin-4-yl-ethoxy)naphthalen-1-yl]-urea;
1-[2-Carbomethoxy-5-(1-methylcyclohex-1-yl)-3-furyl]-3-[4-(2-morpholin-4-yl-ethoxy)naphthalen-1-yl]-urea;
1-[2-Carbomethoxy-5-tert-butyl-3-pyrrolyl]-3-[4-(2-morpholin-4-yl-ethoxy)naphthalen-1-yl]-urea;
1-[2-Methylcarbamoyl-5-tert-butyl-3-pyrrolyl]-3-[4-(2-morpholin-4-yl-ethoxy)naphthalen-1-yl]-urea;
1-[1-Methyl-2-carbomethoxy-5-tert-butyl-3-pyrrolyl]-3-[4-(2-morpholin-4-yl-ethoxy)naphthalen-1-yl]-urea;
1-[2-Carbomethoxy-5-tert-butyl-3-pyrrolyl]-3-[4-(2-(cis-2,6-dimethylmorpholin-4-yl)ethoxy)naphthalen-1-yl]-urea;
1-[2-Methylcarbamoyl-5-tert-butyl-3-pyrrolyl]-3-[4-(2-(trans-2,6-dimethylmorpholin-4-yl)ethoxy)naphthalen-1-yl]-urea;
1-[2-Carbomethoxy-5-tert-butyl-3-pyrrolyl]-3-[4-(2-(2-(methoxymethyl)morpholin-4-yl)ethoxy)naphthalen-1-yl]-urea;
1-[2-Carbomethoxy-5-tert-butyl-3-pyrrolyl]-3-[4-(2-(morpholin-4-yl)-1-methylethoxy)naphthalen-1-yl]-urea;
1-[2-Carbomethoxy-5-tert-butyl-3-pyrrolyl]-3-[4-(2-(1-oxothiomorpholin-4-yl)ethoxy)naphthalen-1-yl]-urea;
1-[2-Methylcarbamoyl-5-tert-butyl-3-pyrrolyl]-3-[4-(2-(1-oxothiomorpholin-4-yl)ethoxy)naphthalen-1-yl]-urea;
1-[1-Methyl-2-carbomethoxy-5-tert-butyl-3-pyrrolyl]-3-[4-(2-(1-oxothiomorpholin-4-yl)ethoxy)naphthalen-1-yl]-urea;
1-[2-Carbomethoxy-5-tert-butyl-3-pyrrolyl]-3-[4-(2-(tetrahydropyran-4-yl)ethoxy)naphthalen-1-yl]-urea;
1-[2-Methylcarbamoyl-5-tert-butyl-3-pyrrolyl]-3-[4-(2-(tetrahydropyran-4-yl)ethoxy)naphthalen-1-yl]-urea;
1-[2-Carbomethoxy-5-tert-butyl-3-pyrrolyl]-3-[4-(2-(1-oxo-tetrahydrothiophen-3-yl)ethoxy)naphthalen-1-yl]-urea;
1-[2-Methylcarbamoyl-5-tert-butyl-3-pyrrolyl]-3-[4-(2-(1-oxo-tetrahydrothiophen-3-yl)ethoxy)naphthalen-1-yl]-urea;
1-[1-Methyl-2-carbomethoxy-5-tert-butyl-3-pyrrolyl]-3-[4-(2-(1-oxo-tetrahydrothiophen-3-yl)ethoxy)naphthalen-1-yl]-urea;
1-[2-Methylcarbamoyl-5-tert-butyl-3-pyrrolyl]-3-[4-(3-morpholin-4-yl-propyl)naphthalen-1-yl]-urea;
1-[2-Carbomethoxy-5-tert-butyl-3-pyrrolyl]-3-[4-(morpholin-4-yl-methyl)naphthalen-1-yl]-urea;
1-[2-Carbomethoxy-5-tert-butyl-3-pyrrolyl]-3-[4-(2-pyridin-4-yl-ethyl)naphthalen-1-yl]-urea;
1-[2-Carbomethoxy-5-tert-butyl-3-pyrrolyl]-3-[4-(3-(morpholin-4-yl)propyn-1-yl)naphthalen-1-yl]-urea;
1-[2-Methylcarbamoyl-5-tert-butyl-3-pyrrolyl]-3-[4-(3-(tetrahydropyran-2-yl-oxy)propyn-1-yl)naphthalen-1-yl]-urea;
1-[2-Methylcarbamoyl-5-tert-butyl-3-pyrrolyl]-3-[4-(3-(tetrahydropyran-2-yl-oxy)butyn-1-yl)naphthalen-1-yl]-urea;
1-[2-Carbomethoxy-5-tert-butyl-3-pyrrolyl]-3-[4-(pyridin4-yl-methoxy)naphthalen-1-yl]-urea;
1-[2-Methylcarbamoyl-5-tert-butyl-3-pyrrolyl]-3-[4-(pyridin4-yl-methoxy)naphthalen-1-yl]-urea;
1-[2-Carbomethoxy-5-tert-butyl-3-pyrrolyl]-3-[4-(2-pyridin-4-yl-ethoxy)naphthalen-1-yl]-urea;
1-[2-Methylcarbamoyl-5-tert-butyl-3-pyrrolyl]-3-[4-(3-pyridin-4-yl-propoxy)naphthalen-1-yl]-urea;
1-[2-Carbomethoxy-5-tert-butyl-3-pyrrolyl]-3-[4-(2-imidazol-1-yl-ethoxy)naphthalen-1-yl]-urea;
1-[2-Carbomethoxy-5-tert-butyl-3-pyrrolyl]-3-[4-(2-(3,4-dimethoxyphenyl)-ethoxy)naphthalen-1-yl]-urea;
1-[2-Methylcarbamoyl-5-tert-butyl-3-pyrrolyl]-3-[4-(2-(3,4-dimethoxyphenyl)-ethoxy)naphthalen-1-yl]-urea;
1-[1-Methyl-2-carbomethoxy-5-tert-butyl-3-pyrrolyl]-3-[4-(2-(3,4-dimethoxyphenyl)-ethoxy)naphthalen-1-yl]-urea;
1-[2-Methylcarbamoyl-5-tert-butyl-3-pyrrolyl]-3-[4-(pyridin-4-yl-methylamino)naphthalen-1-yl]-urea;
1-[2-Carbomethoxy-5-iso-propyl-3-pyrrolyl]-3-[4-(2-morpholin4-yl-ethoxy)naphthalen-1-yl]-urea;
1-[2-Methylcarbamoyl-5-cyclohexyl-3-pyrrolyl]-3-[4-(2-morpholin-4-yl-ethoxy)naphthalen-1-yl]-urea;
1-[5-2-Carbomethoxy-5-(2,2,2-trifluoroethyl)-3-pyrrolyl]-3-[4-(2-morpholin-4-yl-ethoxy)naphthalen-1-yl]-urea;
1-[2-Carbomethoxy-5-(1-methylcycloprop-1-yl)-3-pyrrolyl]-3-[4-(2-morpholin-4-yl-ethoxy)naphthalen-1-yl]-urea;
1-[2-Carbomethoxy-5-(1-methylcyclohex-1-yl)-3-pyrrolyl]-3-[4-(2-morpholin-4-ethoxy)naphthalen-1-yl]-urea;
and their pharmaceutically acceptable derivatives.

The following are preferred compounds of the invention:

1-[2-Carbomethoxy-5-tert-butyl-3-thienyl]-3-[4-(2-morpholin-4-yl-ethoxy)naphthalen-1-yl]-urea;
1-[2-Methylcarbamoyl-5-tert-butyl-3-thienyl]-3-[4-(2-morpholin4-yl-ethoxy)naphthalen-1-yl]-urea;
1-[2-Methylcarbamoyl-5-tert-butyl-3-thienyl]-3-[4-(2-(trans-2,6-dimethylmorpholin-4-yl)ethoxy)naphthalen-1-yl]-urea;
1-[2-Methylcarbamoyl-5-tert-butyl-3-thienyl]-3-[4-(2-(2-dimethylaminomethyldimethylmorpholin-4-yl)ethoxy) naphthalen-1-yl]-urea;
1-[2-Carbomethoxy-5-tert-butyl-3-thienyl]-3-[4-(2-(1-oxothiomorpholin4-yl)ethoxy)naphthalen-1-yl]-urea;
1-[2-Methylcarbamoyl-5-tert-butyl-3-thienyl]-3-[4-(2-(1-oxothiomorpholin-4-yl)ethoxy)naphthalen-1-yl]-urea;
1-[3-Carbomethoxy-5-tert-butyl-2-thienyl]-3-[4-(2-(1-oxothiomorpholin-4-yl)ethoxy)naphthalen-1-yl]-urea;
1-[2-Carbomethoxy-5-tert-butyl-3-thienyl]-3-[4-(2-(tetrahydropyran-4-yl)ethoxy)naphthalen-1-yl]-urea;
1-[2-Methylcarbamoyl-5-tert-butyl-3-thienyl]-3-[4-(2-(tetrahydropyran-4-yl)ethoxy)naphthalen-1-yl]-urea;
1-[3-Carbomethoxy-5-tert-butyl-2-thienyl]-3-[4-(2-(tetrahydropyran-4-yl)ethoxy)naphthalen-1-yl]-urea;
1-[2-Carbomethoxy-5-tert-butyl-3-thienyl]-3-[4-(2-(1-oxo-tetrahydrothiophen-3-yl)ethoxy)naphthalen-1-yl]-urea;
1-[2-Methylcarbamoyl-5-tert-butyl-3-thienyl]-3-[4-(2-(1-oxo-tetrahydrothiophen-3-yl)ethoxy)naphthalen-1-yl]-urea;
1-[2-Carbomethoxy-5-tert-butyl-3-thienyl]-3-[4-(pyridin-4-yl-methoxy)naphthalen-1-yl]-urea;
1-[2-Methylcarbamoyl-5-tert-butyl-3-thienyl]-3-[4-(pyridin-4-yl-methoxy)naphthalen-1-yl]-urea;
1-[2-Carbomethoxy-5-tert-butyl-3-thienyl]-3-[4-(2-imidazol-1-yl-ethoxy)naphthalen-1-yl]-urea;
1-[2-Carbomethoxy-5-tert-butyl-3-thienyl]-3-[4-(2-(3,4-dimethoxyphenyl)-ethoxy)naphthalen-1-yl]-urea;
1-[2-Methylcarbamoyl-5-tert-butyl-3-thienyl]-3-[4-(2-(3,4-dimethoxyphenyl)-ethoxy)naphthalen-1-yl]-urea;
1-[2-Carbomethoxy-5-tert-butyl-3-pyrrolyl]-3-[4-(2-morpholin-4-yl-ethoxy)naphthalen-1-yl]-urea;
1-[2-Methylcarbamoyl-5-tert-butyl-3-pyrrolyl]-3-[4-(2-morpholin-4-yl-ethoxy)naphthalen-1-yl]-urea;
1-[1-Methyl-2-carbomethoxy-5-tert-butyl-3-pyrrolyl]-3-[4-(2-morpholin-4-yl-ethoxy)naphthalen-1-yl]-urea;
1-[2-Carbomethoxy-5-tert-butyl-3-pyrrolyl]-3-[4-(2-(1-oxothiomorpholin-4-yl)ethoxy)naphthalen-1-yl]-urea;
1-[2-Methylcarbamoyl-5-tert-butyl-3-pyrrolyl]-3-[4-(2-(1-oxothiomorpholin-4-yl)ethoxy)naphthalen-1-yl]-urea;
1-[1-Methyl-2-carbomethoxy-5-tert-butyl-3-pyrrolyl]-3-[4-(2-(1-oxothiomorpholin-4-yl)ethoxy)naphthalen-1-yl]-urea;
1-[2-Carbomethoxy-5-tert-butyl-3-pyrrolyl]-3-[4-(2-(tetrahydropyran-4-yl)ethoxy)naphthalen-1-yl]-urea;
1-[2- Methylcarbamoyl -5-tert-butyl-3-pyrrolyl]-3-[4-(2-(tetrahydropyran-4-yl)ethoxy)naphthalen-1-yl]-urea;
1-[2-Carbomethoxy-5-tert-butyl-3-pyrrolyl]-3-[4-(2-(1-oxo-tetrahydrothiophen-3-yl)ethoxy)naphthalen-1-yl]-urea;
1-[2-Methylcarbamoyl-5-tert-butyl-3-pyrrolyl]-3-[4-(2-(1-oxo-tetrahydrothiophen-3-yl)ethoxy)naphthalen-1-yl]-urea;
1-[1-Methyl-2-carbomethoxy-5-tert-butyl-3-pyrrolyl]-3-[4-(2-(1-oxo-tetrahydrothiophen-3-yl)ethoxy)naphthalen-1-yl]-urea;
1-[2-Carbomethoxy-5-tert-butyl-3-pyrrolyl]-3-[4-(pyridin-4-yl-methoxy)naphthalen-1-yl]-urea;
1-[2-Methylcarbamoyl-5-tert-butyl-3-pyrrolyl]-3-[4-(pyridin-4-yl-methoxy)naphthalen-1-yl]-urea;
1-[2-Carbomethoxy-5-tert-butyl-3-pyrrolyl]-3-[4-(2-pyridin4-yl-ethoxy)naphthalen-1-yl]-urea;
1-[2-Carbomethoxy-5-tert-butyl-3-pyrrolyl]-3-[4-(2-imidazol-1-yl-ethoxy) naphthalen-1-yl]-urea;
1-[2-Carbomethoxy-5-tert-butyl-3-pyrrolyl]-3-[4-(2-(3,4-dimethoxyphenyl)-ethoxy) naphthalen-1-yl]-urea;
1-[2-Methylcarbamoyl-5-tert-butyl-3-pyrrolyl]-3-[4-(2-(3,4-dimethoxyphenyl)-ethoxy) naphthalen-1-yl]-urea;
1-[1-Methyl-2-carbomethoxy-5-tert-butyl-3-pyrrolyl]-3-[4-(2-(3,4-dimethoxyphenyl)-ethoxy)naphthalen-1-yl]-urea;
and their pharmaceutically acceptable derivatives.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

All terms as used herein in this specification, unless otherwise stated, shall be understood in their ordinary meaning as known in the art. For example, $C_{1-6}$ alkoxy is a $C_{1-6}$ alkyl with a terminal oxygen, such as methoxy, ethoxy, propoxy, pentoxy and hexoxy. All alkyl groups shall be understood as being branched or unbranched unless otherwise specified. Other more specific definitions are as follows:

The term "aroyl" as used in the present specification shall be understood to mean "benzoyl" or "naphthoyl".

The term "halogen" as used in the present specification shall be understood to mean bromine, chlorine, fluorine or iodine.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—$(C_1–C_4$ alkyl$)_4^+$ salts.

In addition, the compounds of this invention include prodrugs of compounds of the formula (I). Prodrugs include those compounds that, upon simple chemical transformation, are modified to produce a compound of formula (I). Simple chemical transformations include hydrolysis, oxidation and reduction. Specifically, when a prodrug of this invention is administered to a patient, the prodrug may be transformed into a compound of formula (I), thereby imparting the desired pharmacological effect.

General Synthetic Methods

A process of making a compound of the formula(I) below can be made by the following general scheme:

Step 1 involves reacting and aminoheterocycle of the formula (II): $Ar_1$—$NH_2$ with phenyl chloroformate to form a carbamate compound of the formula (V):

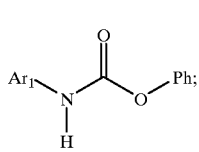

(V)

Step 2 is reacting the carbamate of the formula (V) from step 1 with an aromatic amine of the formula (IV):

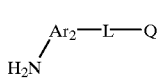

(IV)

to form a compound of the formula (I)

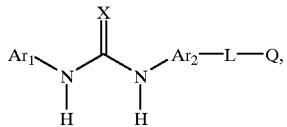

wherein $Ar_1$, $Ar_2$, L, Q and X are as defined hereinabove.

More particularly, the compounds of the invention may be prepared by Method A–P as illustrated below. The method of preparation will vary depending on the particular compound desired and the proper method chosen will be apparent to one of ordinary skill in the art.

Desired intermediate aminoheterocycles (2), of the formula II, can be prepared by methods known in the art and described in the literature. The method used to produce an aminoheterocycle of formula II will depend on the nature of the desired heterocycle. Some general methods are illustrated in the schemes below. Compounds OCN—$Ar_2$—L—Q or $NH_2$—$Ar_2$—L—Q may be commercially available, or may be prepared by methods known to those skilled in the art. Illustrative examples are contained in the Synthetic Procedures section below.

The examples that follow are illustrative and, as recognized by one skilled in the art, particular reagents or conditions could be modified as needed for individual compounds. Intermediates used in the schemes below are either commercially available or easily prepared from commercially available materials by those skilled in the art.

Synthetic Procedures

Preparation 1-[2-carbomethoxy-5-alkyl-3-thienyl]-3-[aryl]-urea (1)

Method A

Methyl 5-alkyl-3-aminothiophene-2-carboxylates (2) can be prepared from the base catalyzed condensation of methyl thioglycolate (3) and 2-alkyl-2-chloroacrylonitrile (4). The preferred base is sodium methoxide. The preferred solvent is methanol and the preferred reaction temperatures are between 50–90° C. Purification of the product can be accomplished by recrystallization, distillation or silica gel chromatography. This 3-aminothiophene (2) can be treated with phenyl chloroformate in the presence of a base. The preferred base is pyridine or triethylamine and the preferred solvent is THF. The resultant thiophene phenyl carbamate (5) is reacted with an aromatic amine (6) in DMSO with a base, such as triethylamine, to give the urea product (1) which can be purified by recrystallization or silica gel chromatography.

Method A:

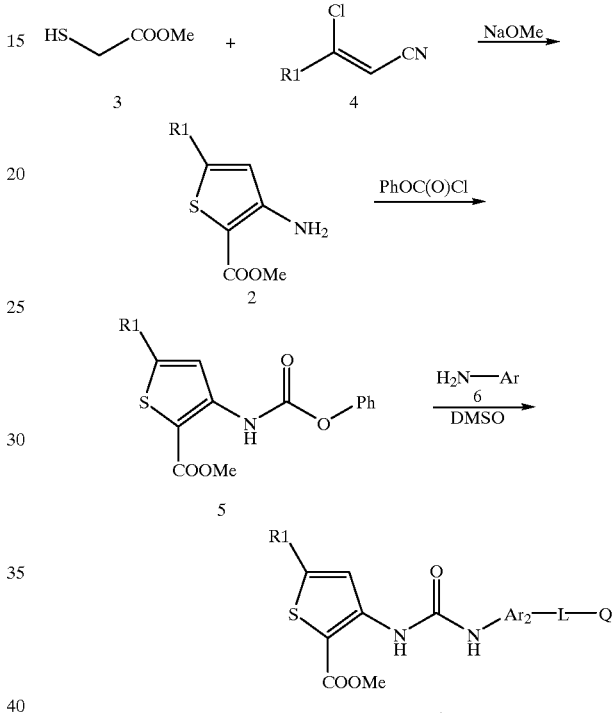

Method B

3-Aminothiophene (2) is dissolved in methylene chloride and aqueous sodium bicarbonate and cooled to 0° C. Phosgene is added and the thiophene isocyanate (7) is separated from the aqueous layer, dried and reacted with an aromatic amine (6) and a base, such as triethylamine, in a non-protic solvent, such as THF, to give the urea product (1).

Method B:

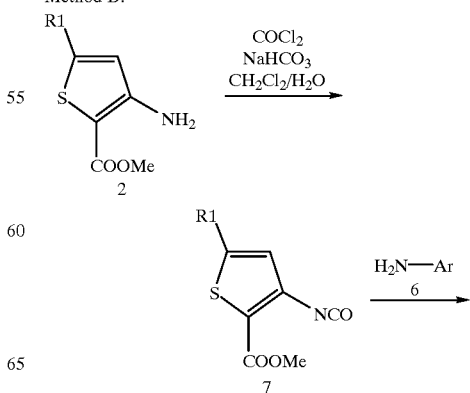

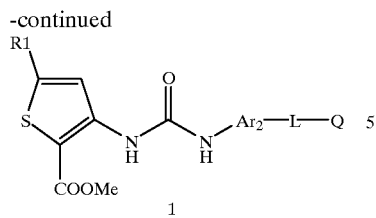

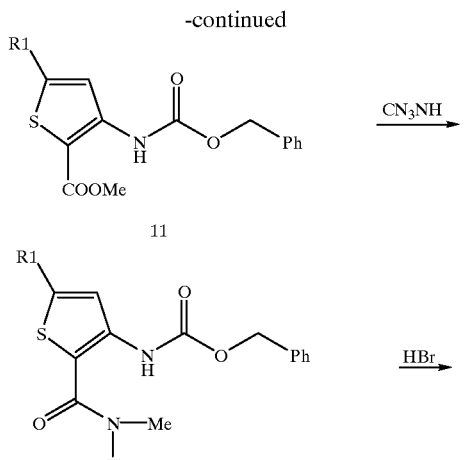

Method C

Aromatic amine (6) is dissolved in methylene chloride and aqueous sodium bicarbonate and cooled to 0° C. Phosgene is added and the aromatic isocyanate (8) is separated from the aqueous layer, dried and reacted with the thiophene amine (2) to give the urea product (1).

Method C:

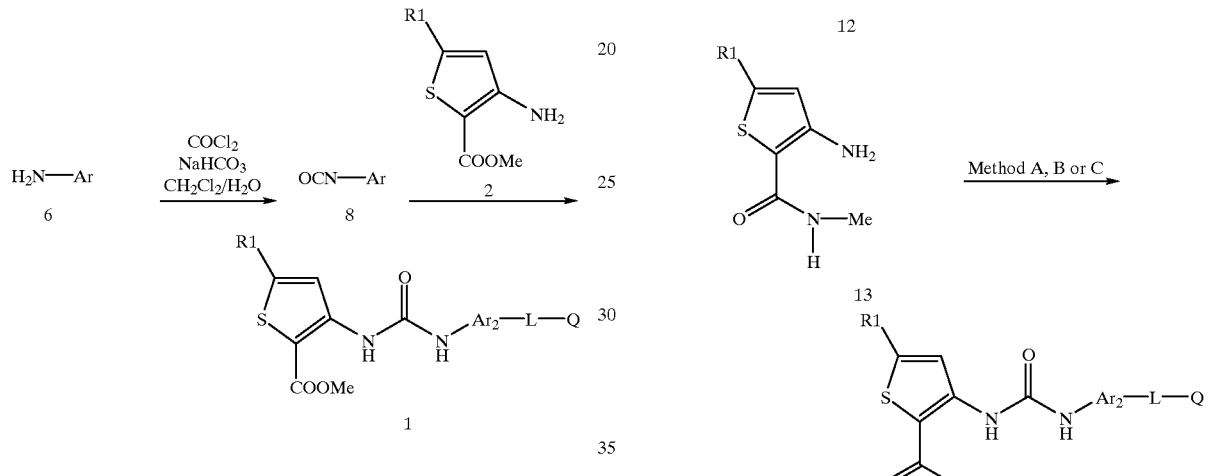

Preparation of 1-[2-methylcarbamoyl-5-alkyl-3-thienyl]-3-[aryl]-urea (10)

Method D

2-Methylcarbamoyl-5-alkyl-3-aminothiophenes (13) can be prepared from methyl 5-alkyl-3-aminothiophene-2-carboxylates (2) by reacting the amino group with benzyl chloroformate in a non-protic solvent, such as toluene, and a base, such as sodium carbonate. The resultant methyl 3-(N-carbobenzyloxyamino)-5-alkyl-thiophene-2-carboxylate (11) can be treated with methylamine and NaCN in a protic solvent, such as methanol, in a sealed vessel at elevated temperatures. The preferred temperatures are between 50–90° C. Purification of 2-methylcarbamoyl-5-alkyl-3-(N-carbobenzyloxyamino)thiophene (12) can be accomplished with silica gel chromatography. Removal of the carbobenzyloxy group can be accomplished with HBr in acetic acid to furnish amine (13). Urea formation with this amine can be accomplished by Methods A, B or C, listed above, to give 1-[2-methylcarbamoyl-5-alkyl-3-thienyl]-3-[aryl]-urea (10).

Method D:

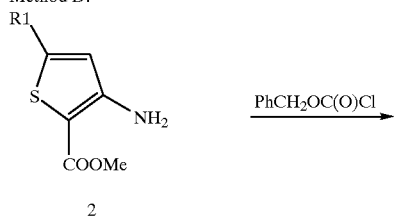

Preparation of 1-[2-(N-acetylaminomethyl)-5-alkyl-3-thienyl]-3-[aryl]-urea (14).

Method E

1-[2-(Aminomethyl)-5-alkyl-3-thienyl]-3-[aryl]-urea (15) can be prepared by treatment of 1-[2-carbamoyl-5-alkyl-3-thienyl]-3-[aryl]-urea (16), which can be prepared according to Method D by replacing methylamine with ammonia, with a hydride reducing agent, such as borane in THF in a non-protic solvent, such as THF, at elevated temperatures, such as between 50–90° C., and purification by silica gel chromatography. An amide (16) can be prepared by coupling of this amine with an N-protected glycine, such as N-carbo-tert-butoxyglycine (17), with standard peptide forming reagents, such as dicyclohexylcarbodiimide and hydroxybenzotriazole, in a non-protic solvent, such as THF, and purification of the product with silica gel chromatography. Formation of the N-acetyl product (14) can be accomplished by treatment of (16) with acid to furnish amine (17) and subsequent reaction with an acylating reagent, such as acetyl chloride or acetic anhydride, in a non-protic solvent, such as THF, and purification by silica gel chromatography.

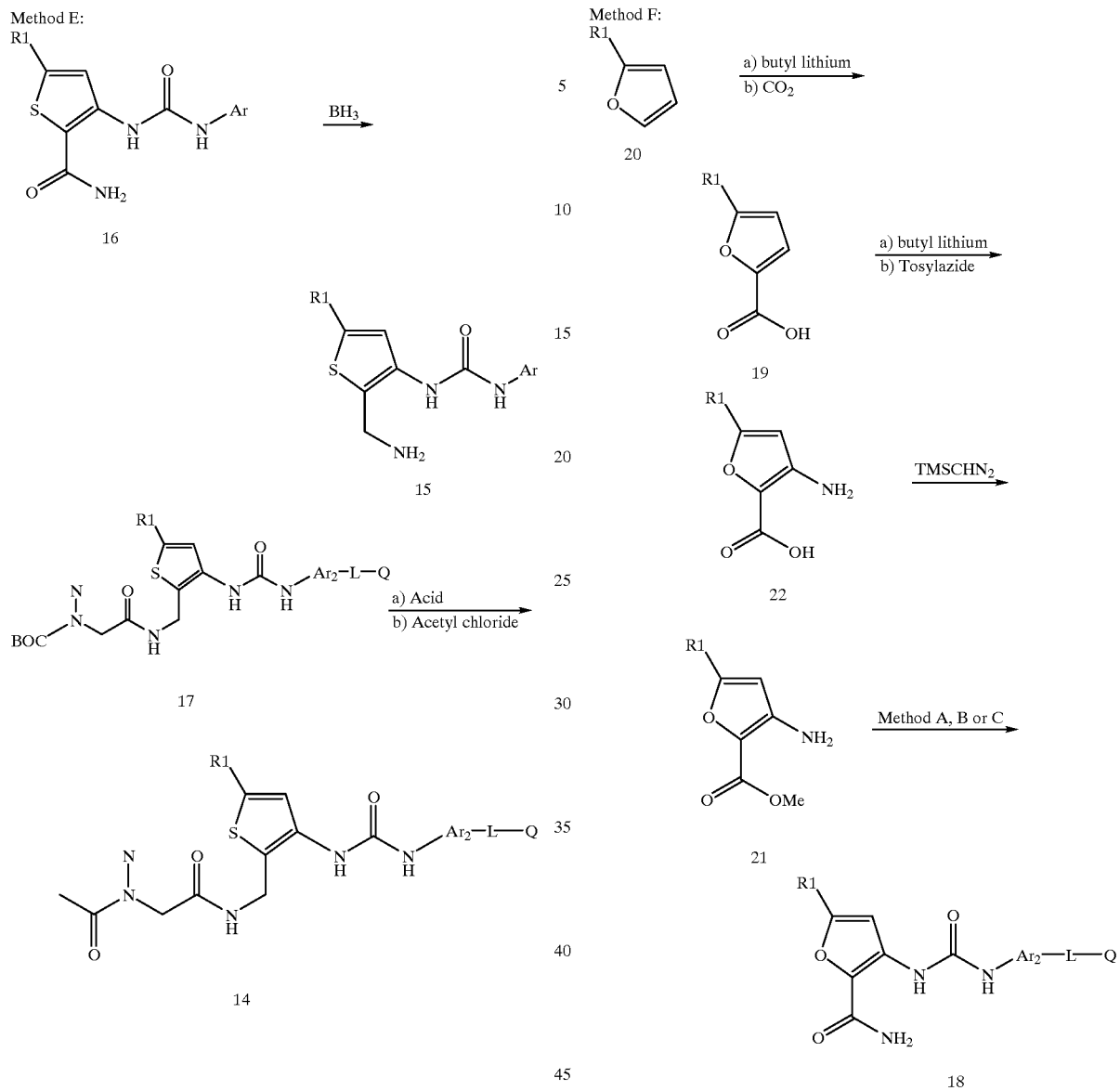

Preparation of 1-[2-carbomethoxy-5-alkyl-3-furyl]-3-[aryl]-urea (18).

Method F

5-Alkyl-furan-2-carboxylate (19) can be prepared by treatment of 2-alkyl-furan (20) with a strong base, such as butyl lithium, in a non-protic solvent, such as THF, at temperatures −78 −0° C. and quenching with carbon dioxide. Methyl 5-alkyl-3-amino-furan-2-carboxylate (21) can be prepared by treatment of 5-alkyl-furan-2-carboxylate (19) with a strong base, such as butyl lithium, in a non-protic solvent, such as THF, at temperatures −78 −0° C. and quenching with tosylazide. The carboxylic acid can be esterified with $TMSCHN_2$ in methanol to give methyl 5-alkyl-3-amino-furan-2-carboxylate (22). Urea formation with this amine can be accomplished by Method A, B or C, as described above, to provide 1-[2-carbomethoxy-5-alkyl-3-furyl]-3-[aryl]-urea (18).

Preparation of 1-[2-carbomethoxy-5-alkyl-3-pyrrolyl]-3-[aryl]-urea (23).

Method G

Methyl 5-alkyl-pyrrole-2-carboxylate (24) can be prepared by treatment of methyl pyrrole-2-carboxylate (25) with a Lewis acid, such as $AlCl_3$, in a non-protic solvent, such as dichloromethane, and a chloroalkane, such as 2-chloro-2-methylproprane. Nitration of this product (24) can be accomplished with fuming nitric acid to afford methyl 5-alkyl-3-nitropyrrole-2-carboxylate (26) which upon hydrogenation with a palladium catalyst in a protic solvent, such as methanol, and purification with silica gel chromatography would afford methyl 5-alkyl-3-aminopyrrole-2-carboxylate (27). Urea formation with this amine by Method A, B or C, as described above, would furnish 1-[2-carbomethoxy-5-alkyl-3-pyrrolyl]-3-[aryl]-urea (23).

Method G:

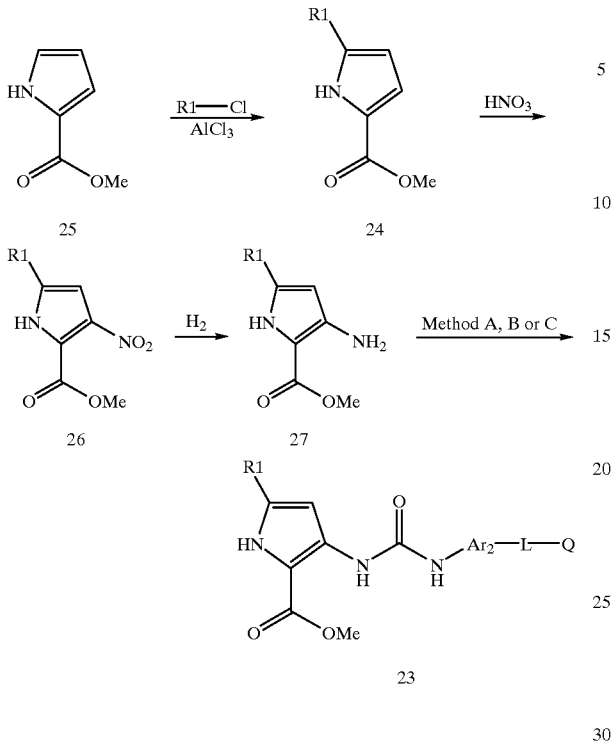

Preparation of 1-[²-methylcarbamoyl-5-alkyl-3-pyrrolyl]-3-[aryl]-urea (28)

Method H

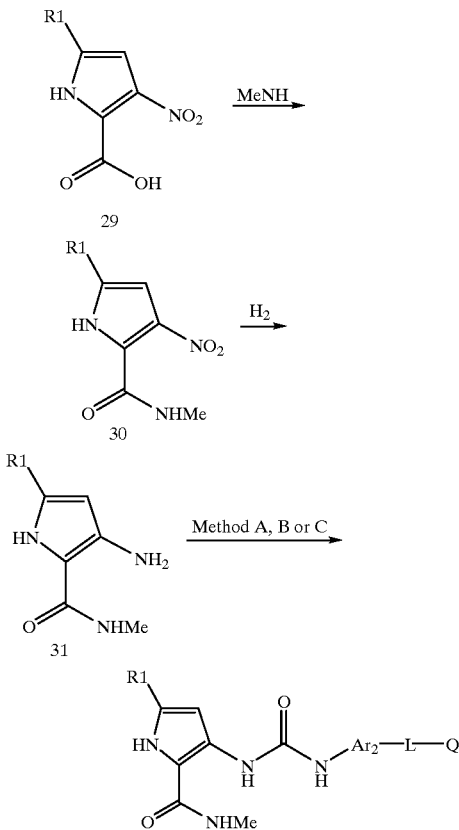

5-Alkyl-3-nitropyrrole-2-carboxylate (29) can be prepared from methyl 5-alkyl-3-nitropyrrole-2-carboxylate (26), as prepared above, by treatment with alkali, such as sodium hydroxide, in solvent mixtures, such as THF, methanol and water, at temperatures between 50–90° C. Purification of the product can be accomplished by trituration or silica gel chromatography. Conversion of 5-alkyl-3-nitropyrrole-2-carboxylate (29) to 2-methylcarbamoyl-5-alkyl-3-nitropyrrole (30) can be accomplished by treatment with methylamine and amide forming reagents, such as EDCI, in non-protic solvents, such as THF and DMF. 2-Methylcarbamoyl-5-alkyl-3-aminopyrrole (31) can be prepared by reduction of the nitro group by hydrogen in the presence of a palladium catalyst in a non-protic solvent, such as ethyl acetate. Urea formation with this amine (31) can be accomplished by Method A, B or C, as described above, to furnish 1-[2-methylcarbamoyl-5-alkyl-3-pyrrolyl]-3-[aryl]-urea 28).

Preparation of 1-[1-methyl-2-carbomethoxy-5-alkyl-3-pyrrolyl]-3-[aryl]-urea (32)

Method I

Methyl 1-methyl-5-alkyl-3-nitropyrrole-2-carboxylate (33) can be prepared by treating methyl 5-alkyl-3-nitropyrrole-2-carboxylate (26) with alkali, such as NaOH, in a mixture of a non-protic solvent, such as methylene chloride, and water with a phase transfer catalyst, such as benzyltributylammonium bromide, and a methylating agent, such as dimethyl sulfate. The preferred temperature is between 0–25° C. Purification of methyl 1-methyl-5-alkyl-3-nitropyrrole-2-carboxylate (33) can be accomplished by silica gel chromatography. Reduction of the nitro group can be completed with hydrogen and a palladium catalyst, such as palladium on carbon. Urea formation with this amine (34) can be accomplished by Method A, B or C, as described above, to furnish 1-[1-methyl-2-carbomethoxy-5-alkyl-3-pyrrolyl]-3-[aryl]-urea (32).

Method H:

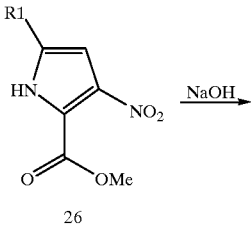

Method I:

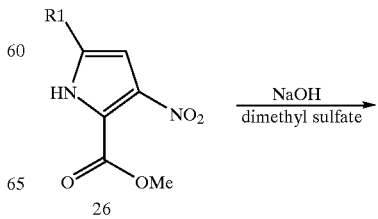

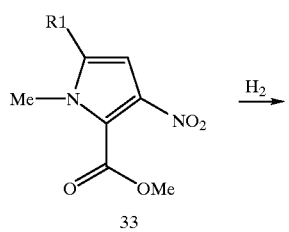

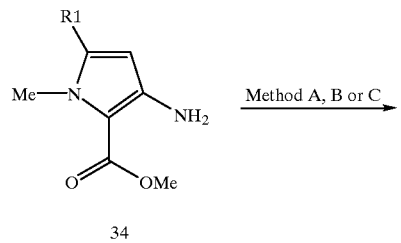

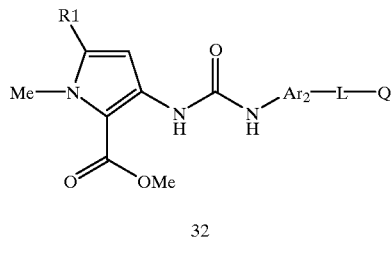

Preparation 1-[2-carbomethoxy-5-tert-butyl-3-thienyl]-3-[aryl]-urea (35)

Method J

2-Carbomethoxy-5-tert-butyl-3-aminothiophene (36) can be prepared by the condensation of methyl cyanoacetate (37), 3,3-dimethylbutraldehyde (38) and sulfur in a non-protic base, such as DMF, and a base, such as triethylamine. Purification of the product can be accomplished with silica gel chromatography. Urea formation with this amine (36) can be accomplished as described by Method A, B or C, as described above, to furnish 1-[2-carbomethoxy-5-tert-butyl-3-thienyl]-3-[aryl]-urea (35).

Method J:

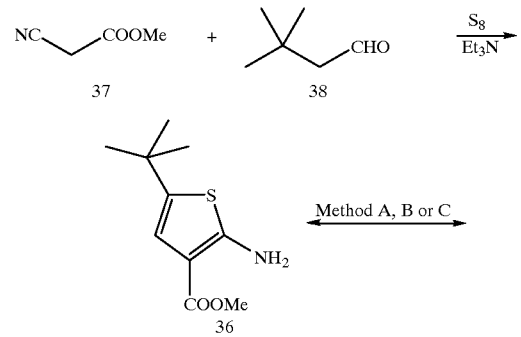

Preparation of $H_2N-Ar_2-L-Q$ (IV)=1-amino-4-(2-(morpholin-4-yl)ethoxy)naphthalene (39)

Method K

4-Amino-1-naphthol hydrochloride (40) can be neutralized with a base, such as n-butyl lithium, in a non-protic solvent, such as THF, and reacted with di-tert-butyl dicarbonate ((BOC)$_2$O) at temperatures between −78 −25° C. The product, 4-tert-butyloxycarbonylamino-1-naphthol (41) can be alkylated with 4-(2-chloroethyl)morpholine hydrochloride in a non-protic solvent, such as acetonitrile, with a base, such as powdered potassium carbonate, at temperatures between 60–80° C. Purification of the product 4-tert-butyloxycarbonylamino-1-(2-(morpholin-4-yl)ethoxy)naphthalene (42) can be accomplished by silica gel chromatography. Removal of the BOC-protecting group can be accomplished with HCl in a non-protic solvent, such as dioxane, to furnish 1-amino-4-(2-(morpholin-4-yl)ethoxy)naphthalene (39) as the hydrochloride salt.

Method K:

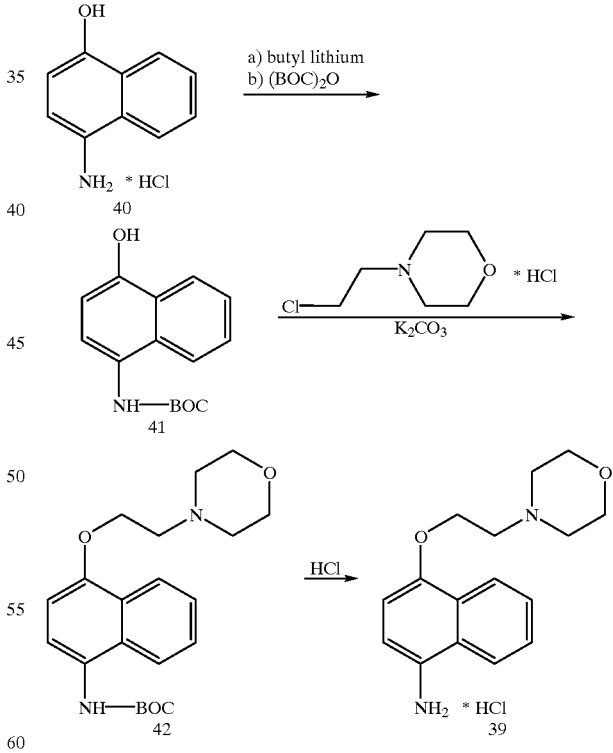

Preparation of $H_2N-Ar_2-L-Q$ (IV)=1-amino-4-(pyridin-4-yl-methoxy)naphthalene (43)
Method L
4-tert-Butyloxycarbonylamino-1-naphthol (41) can be alkylated with 4-chloromethylpyridine hydrochloride in a non-protic solvent, such as acetonitrile, with a base, such as powdered potassium carbonate, at temperatures between 60–80° C. Purification of the product 4-tert-butyloxycarbonylamino-1-(pyridin-4-yl-methyl)naphthalene (44) can be accomplished by silica gel chromatography. Removal of the BOC-protecting group can be accomplished with HCl in a non-protic solvent, such as dioxane, to provide 1-amino-4-(pyridin-4-yl-methoxy)naphthalene (43) as the hydrochloride salt.

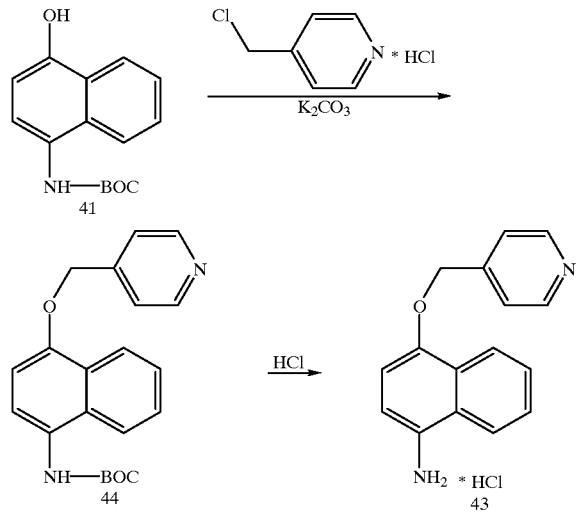

Preparation of H$_2$N—Ar$_2$—L—Q (IV)=1-amino-4-(2-(1-oxo-thiomorpholin-4-yl)ethoxy)naphthalene (45)

Method M 4-tert-Butyloxycarbonylamino-1-naphthol (41) can be alkylated with 1-bromo-2-chloroethane in a non-protic solvent, such as acetonitrile, with a base, such as powdered potassium carbonate, at temperatures between 60–80° C. Purification of the product 4-tert-butyloxycarbonylamino-1-(2-chloroethoxy)naphthalene (46) can be accomplished by silica gel chromatography. Conversion of 4-tert-butyloxycarbonylamino-1-(2-chloroethoxy)naphthalene (46) to 4-tert-butyloxycarbonylamino-1-(2-iodooethoxy)naphthalene (47) can be accomplished with the NaI in a non-protic solvent, such as acetone, at elevated temperatures. Treatment of (47) with thiomorpholine in a non-protic solvent, such as DMF, and a base, such as di-iso-propyl-ethylamine (DIPEA), at room temperature can provide 4-tert-butyloxycarbonylamino-1-(2-(thiomorpholin-4-yl)ethoxy)naphthalene (48). Oxidation of the thiomorpholine to yield 4-tert-butyloxycarbonylamino-1-(2-(1-oxo-thiomorpholin4-yl)ethoxy)naphthalene (49) can be accomplished with sodium periodate in a protic solvent, such as ethanol, at temperatures between 0–25° C. Purification of the product can be performed by silica gel chromatography. Removal of the BOC-protecting group of (49) can be executed with trifluoroacetic acid in a non-protic solvent, such as methylene chloride, to furnish 1-amino-4-(2-(1-oxo-thiomorpholin-4-yl)ethoxy)naphthalene (45).

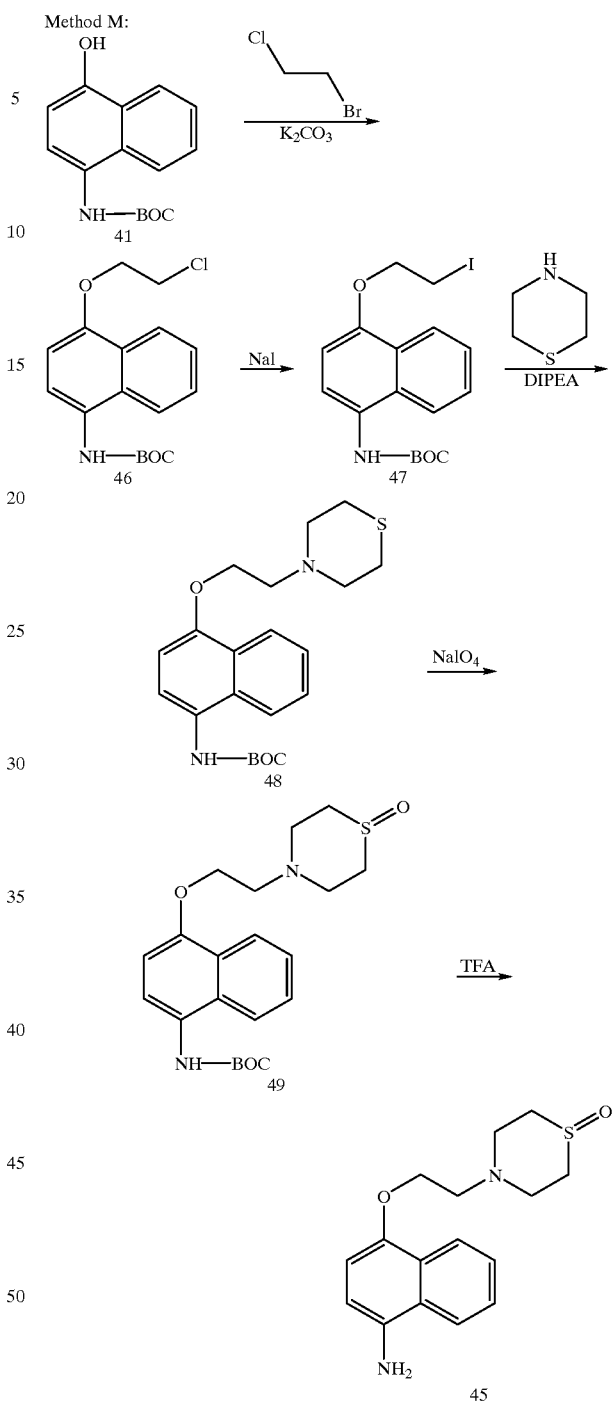

Preparation of H$_2$N—Ar$_2$—L—Q (IV)=1-amino-4-(3,4-dimethoxyphenyl)methoxy)naphthalene (50)

Method N

4-Amino-1-naphthol hydrochloride (40) can be neutralized with a base, such as aqueous sodium bicarbonate, in a non-protic solvent, such as ethyl acetate, and reacted 3,4-dimethoxybenzyl alcohol, triphenyl phosphine and diethyl azodicarboxylate (DEADC) in a non-protic solvent, such as THF, at temperatures between 0–25° C. Purification of 1-amino-4-(3,4-dimethoxyphenyl)methoxy)naphthalene (50) can be performed by silica gel chromatography.

Method N:

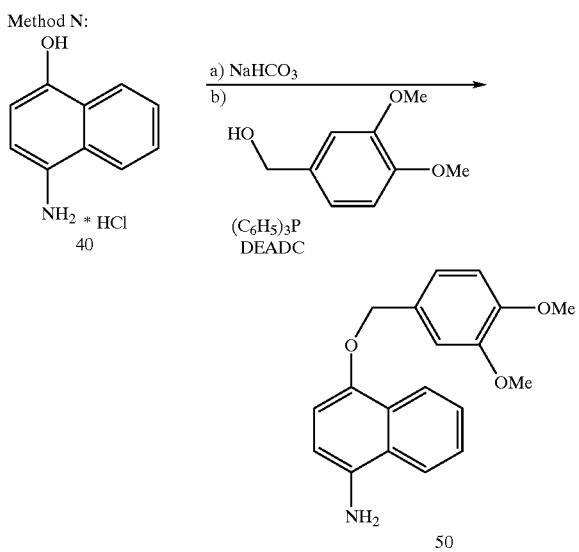

Preparation of (1) wherein Ar₂—L—Q=3-(tetrahydopyran-2-yl-oxy)propyn-1-yl)naphthal-1-ene (51) Method O Tetrahydro-2-(2-propynyloxy)-2H-pyran (52) can be treated with a strong base, such as n-butyl lithium in a non-protic solvent, such as THF, at temperatures between −78–25° C. and quenched with tributyltin chloride to furnish tributyltin derivative (53). Coupling of (53) and bromonaphthalene urea (54), prepared as described in Method A, B or C using 1-amino-4-bromonaphthalene as IV, in a non-protic solvent, such as toluene, in the presence of BHT and a palladium (0) catalyst, such as tetrakis(triphenylphosphine) palladium (0), at temperatures between 100–110° C. would furnish, after purification by silica gel chromatography, product (51).

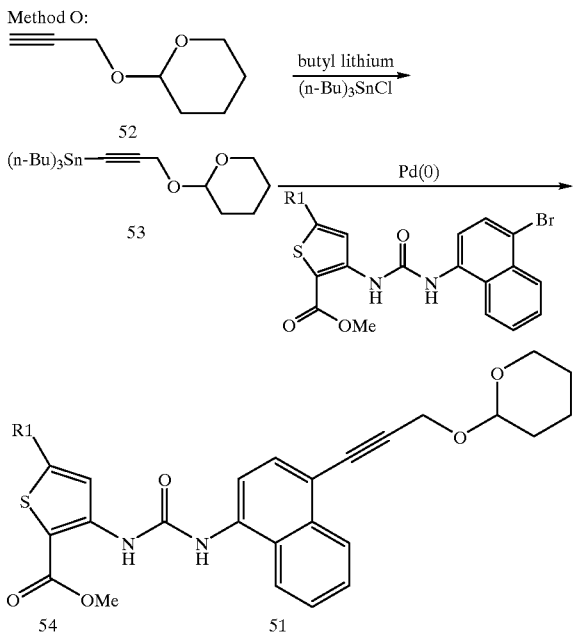

Methods of Therapeutic Use

The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula (I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties
Inhibition of TNF Production in THP Cells

The inhibition of cytokine production can be observed by measuring inhibition of TNFα in lipopolysaccharide stimulated THP cells. All cells and reagents are diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay is performed under sterile conditions; only test compound preparation is non-sterile. Initial stock solutions are made in DMSO followed by dilution into RPMI 1640 2-fold higher than the desired final assay concentration. Confluent THP.1 cells ($2\times10^6$ cells/ml, final conc.; American Type Culture Company, Rockville, Md.) are added to 96 well polypropylene round bottomed culture plates (Costar 3790; sterile) containing 125 μl test compound (2 fold concentrated) or DMSO vehicle (controls, blanks). DMSO concentration should not exceed 0.2% final. Cell mixture is allowed to preincubate for 30 min, 37° C., 5% $CO_2$ prior to stimulation with lipopolysaccharide (LPS; 1 μg/ml final; Siga L-2630, from *E.coli* serotype 0111.B4; stored as 1 mg/ml stock in endotoxin screened distilled $H_2O$ at –80° C.). Blanks (unstimulated) receive $H_2O$ vehicle; final incubation volume is 250 μl. Overnight incubation (18–24 hr) proceeds as described above. Assay is to be terminated by centrifuging plates 5 min, room temperature, 1600 rpm (4033 g); supernatants are then transferred to clean 96 well plates and stored –80° C. until analyzed for human TNFα by a commercially available ELISA kit (Biosource #KHC3015, Camarillo, Calif.). Data is analyzed by non-linear regression (Hill equation) to generate a dose response curve using SAS Software System (SAS institute, Inc., Cary, N.C.). The calculated IC50 value is the concentration of the test compound that caused a 50% decrease in the maximal TNFα production.

Preferred compounds of the invention will have an activity wherein the $IC_{50}<10$ μM in this assay.

Inhibition of Other Cytokines

By similar methods using peripheral blood monocytic cells, appropriate stimuli, and commercially available ELISA kits for a particular cytokine, inhibition of IL-1β, GM-CSF, IL-6 and IL-8 can be demonstrated by preferred compounds.

What is claimed is:

1. A Compound of the formula (I):

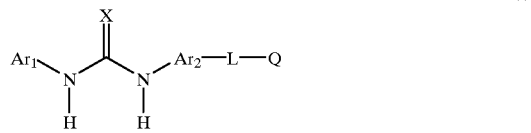

wherein:

$Ar_1$ is selected from the group consisting of pyrrole and thiophene; and wherein $Ar_1$ may be substituted by one or more $R_1, R_2$ or $R_3$;

$Ar_2$ is:

naphthyl optionally substituted with one to three $R_{10}$ groups;

L is a $C_{1-10}$ saturated or unsaturated branched or unbranched carbon chain; wherein one or more methylene groups are optionally independently replaced by O,N or S; wherein L is optionally independently substituted with 0–2 oxo groups or one or more $C_{1-4}$ branched or unbranched alkyl which may be substituted by one or more halogen atoms;

Q is pyridine optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-$S(O)_m$ and phenylamino wherein the phenyl ring is optionally substituted with one to two groups selected from the group consisting of halogen, $C_{1-6}$ alkyl and $C_{1-6}$ alkoxy;

$R_1$ is selected from the group consisting of:

a) $C_{3-10}$ branched or unbranched alkyl, which may optionally be partially or fully halogenated, and optionally substituted with one to three phenyl, naphthyl or heterocyclyl groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocyclyl, selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkoxy which is optionally partially or fully halogenated, $NH_2C(O)$ and di($C_{1-3}$)alkylaminocarbonyl;

b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;

c) $C_{3-10}$ branched alkenyl which may optionally be partially or fully halogenated, and which optionally be substituted with one to three $C_{1-5}$ branched or unbranched alkyl, phenyl, naphthyl or heterocyclyl groups, with each such heterocyclyl group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclyl group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkoxy which is optionally partially or fully halogenated, $NH_2C(O)$ and mono- or di($C_{1-3}$)alkylaminocarbonyl;

d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

e) cyano; and, f) methoxycarbonyl, ethoxycarbonyl and propoxycarbonyl;

$R_2$ is selected from the group consisting of:
hydrogen, $C_{1-6}$ branched or unbranched alkyl which may optionally be partially or fully halogenated, acetyl, aroyl, $C_{1-4}$ branched or unbranched alkoxy which may optionally be partially or fully halogenated, halogen, methoxycarbonyl and phenylsulfonyl;

$R_3$ is:
halogen, $—COOR_4$, $—CN$, $—CONR_5R_6$ or $—CH_2NHR_7$;
$R_4$ is hydrogen or $C_{1-4}$-alkyl;
$R_5$ is hydrogen;
$R_6$ is methyl;
$R_7$ is hydrogen, methyl or $—C(O)R_8$;
$R_8$ is hydrogen or methyl optionally substituted by $N(R_9)_2$ or $COOR_9$;
$R_9$ is $C_{1-6}$-alkyl;
$R_{10}$ is selected from the group consisting of:
a $C_{1-6}$ branched or unbranched alkyl which may optionally be partially or fully halogenated, acetyl, aroyl, $C_{1-4}$ branched or unbranched alkoxy which may optionally be partially or fully halogenated, halogen, methoxycarbonyl and phenylsulfonyl;

m is 0, 1 or 2;
r is 0, 1 or 2;
t is 0, 1 or 2;
X is O or S and
pharmaceutically acceptable derivatives thereof.

2. The Compound according to claim 1 wherein $Ar_1$ is selected from the group consisting of:

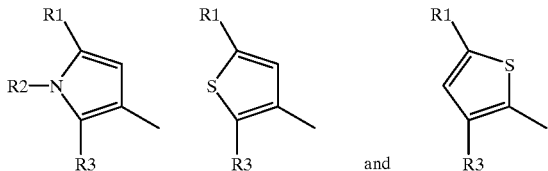

3. A compound according to claim 2 wherein $Ar_2$ is naphthyl, tetrahydronaphthyl, indanyl or indenyl.

4. A compound according to claim 3 wherein $Ar_2$ is naphthyl.

5. A compound according to claim 4 wherein
$Ar_2$ is 1-naphthyl;
L is a $C_{1-6}$ saturated or unsaturated branched or unbranched carbon chain wherein
one or more methylene groups are optionally independently replaced by O,N or S; wherein L is optionally independently substituted with 0–2 oxo groups and one or more $C_{1-4}$ branched or unbranched alkyl which may be substituted by one or more halogen atoms;
$R_1$ is $C_{1-4}$ alkyl branched or unbranched, cyclopropyl or cyclohexyl which may optionally be partially or fully halogenated and which may optionally be substituted with one to three $C_{1-3}$ alkyl groups; and
$R_3$ is $—COOR_4$, $—CN$, $—CONR_5R_6$ or $—CH_2NHR_7$.

6. A compound according to claim 5 wherein L is a $C_{1-5}$ saturated carbon chain wherein one or more methylene groups are optionally independently replaced by O,N or S; wherein said linking group is optionally substituted with 0–2 oxo groups and one or more $C_{1-4}$ branched or unbranched alkyl which may be substituted by one or more halogen atoms; and
X is O.

7. A compound according to claim 6 wherein L is propoxy, ethoxy or methoxy each being optionally substituted with 0–2 oxo groups and one or more $C_{1-4}$ branched or unbranched alkyl which may be substituted by one or more halogen atoms.

8. A compound according to claim 7 wherein L is ethoxy optionally substituted with an oxo group and one or more $C_{1-4}$ branched or unbranched alkyl which may be substituted by one or more halogen atoms.

9. A compound according to claim 6 wherein L is methyl or propyl each being optionally substituted with 0–2 oxo groups and one or more $C_{1-4}$ branched or unbranched alkyl which may be substituted by one or more halogen atoms.

10. A compound according to claim 6 wherein L is $C_{3-5}$ acetylene optionally substituted with 0–2 oxo groups and one or more $C_{1-4}$ branched or unbranched alkyl which may be substituted by one or more halogen atoms.

11. A compound according to claim 6 wherein L is methylamino optionally substituted with an oxo group and one or more $C_{1-4}$ branched or unbranched alkyl which may be substituted by one or more halogen atoms.

12. A compound according to claim 5 wherein
$Ar_1$ is selected from the group consisting of 5-tert-butyl-3-thienyl and 5-tert-butyl-3-pyrrolyl each optionally substituted by $R_1$ or $R_3$ as defined hereinabove in claim 5.

13. A compound selected from the group consisting of:
1-[2-Carbomethoxy-5-tert-butyl-3-thienyl]-3-[4-(pyridin-4-yl-methoxy)naphthalen-1-yl]-urea;
1-[2-Methylcarbamoyl-5-tert-butyl-3-thienyl]-3-[4-(pyridin-4-yl-methoxy)naphthalen-1-yl]-urea;
1-[2-Carbomethoxy-5-tert-butyl-3-pyrrolyl]-3-[4-(pyridin-4-yl-methoxy)naphthalen-1-yl]-urea;
1-[2-Methylcarbamoyl-5-tert-butyl-3-pyrrolyl]-3-[4-(pyridin-4-yl-methoxy)naphthalen-1-yl]-urea;
1-[2-Carbomethoxy-5-tert-butyl-3-pyrrolyl]-3-[4-(2-pyridin-4-yl-ethoxy)naphthalen-1-yl]-urea
and pharmaceutically acceptable derivatives thereof.

14. A method of treating a disease mediated directly or indirectly by cytokines wherein said disease is selected from the group consisting of osteoporosis and Alzheimer's disease said method comprises administering to a patient in need of such treatment a therapeutically effective amount of a compound according to claim 1.

15. A method of treating a neutrophil-mediated disease selected from the group consisting of stroke, myocardial infarction, thermal injury, adult respiratory distress syndrome (ARDS), multiple organ injury secondary to trauma, acute glomerulonephritis, dermatoses with acute inflammatory components, acute purulent meningitis and necrotizing entrerocolitis, said method comprises administering to a patient in need of such treatment a therapeutically effective amount of a compound according to claim 1.

16. A process of making a compound of the formula (I) according to claim 1

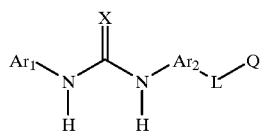
(I)

wherein $Ar_1$, $Ar_2$, L and Q are defined as in claim 1, and X is O;

comprising:

(a) reacting an aminoheterocycle of the formula (II): $Ar_1$-$NH_2$ with phenyl chloroformate in a suitable solvent in the presence of a suitable base to form a carbamate compound of the formula (V):

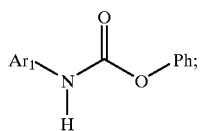
(V)

(b) reacting the carbamate of the formula (V) from step (a) with an arylamine of the formula (IV) in a suitable polar solvent in the presence of a suitable base:

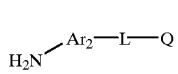
(IV)

to form a compound of the formula (I).

17. A pharmaceutical composition comprising a pharmaceutically effective amount of the compound according to claim 1.

18. A method of treating an inflammatory disease selected from the group consisting of osteoarthritis, multiple sclerosis, Guillain-Barre syndrome, Crohn's disease, ulcerative colitis, psoriasis, graft versus host disease, systemic lupus erythematosus and diabetes, which comprises administering to a patient in need of such treatment a therapeutically effective amount of a compound according to claim 1.

19. A method of treating an autoimmune disease selected from the group consisting of rheumatoid arthritis, toxic shock syndrome, diabetes and inflammatory bowel disease which comprises administering to a patient in need of such treatment a therapeutically effective amount of a compound according to claim 1.

20. A method of treating acute or chronic pain which comprises administering to a patient in need of such treatment a therapeutically effective amount of a compound according to claim 1.

* * * * *